US009211347B2

(12) United States Patent
Uc et al.

(10) Patent No.: US 9,211,347 B2
(45) Date of Patent: Dec. 15, 2015

(54) METHOD OF DELIVERING VECTORS TO PANCREAS AND LUNGS BY CANNULATING THE AORTA

(71) Applicant: University of Iowa Research Foundation, Iowa City, IA (US)

(72) Inventors: Aliye Uc, Iowa City, IA (US); Paul B. McCray, Iowa City, IA (US); Beverly L. Davidson, Iowa City, IA (US); Abhay Divekar, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/030,731

(22) Filed: Sep. 18, 2013

(65) Prior Publication Data

US 2014/0081240 A1 Mar. 20, 2014

Related U.S. Application Data

(60) Provisional application No. 61/702,600, filed on Sep. 18, 2012, provisional application No. 61/792,901, filed on Mar. 15, 2013.

(51) Int. Cl.
*A61K 48/00* (2006.01)
(52) U.S. Cl.
CPC .................. *A61K 48/0075* (2013.01)
(58) Field of Classification Search
CPC .................................................. A61K 48/0075
See application file for complete search history.

(56) References Cited

U.S. PATENT DOCUMENTS 5,139,941 A 8/1992 Muzyczka et al.

OTHER PUBLICATIONS

Kröger et al. (Annals of the New York Academy of Sciences. Jun. 1999; 880: 374-378).*
Sailer et al. (J Gene Med. 2002; 4: 150-160).*
Jimenez et al. (Diabetologia. 2011; 54: 1075-1086).*
Bevan et al. (Molecular Therapy. Published online Aug. 2, 2011; 19(11): 1971-1980).*
Goldman et al. (JAMA. Dec. 6, 1985;254(21):3061-2).*
Abu-El-Haija et al., "A Novel Method for Delivery of AAV Gene Transfer Vectors to the Pig Pancreas", Peds Research Day, University of Iowa Hospitals and Clinics, Iowa City, IA, Poster, 1 page and Abstract, 1 page (Mar. 22, 2011).
Abu-El-Haija et al., "Pancreatic damage in fetal and newborn cystic fibrosis pigs involves the activation of inflammatory and remodeling pathways", *Am. J. Pathol 181*(2), 499-507 (2012).
Ayuso et al., "In vivo gene transfer to pancreatic beta cells by systemic delivery of adenoviral vectors", *Hum Gene Ther 15* (8) 805-812 (2004).

Burghardt et al., "Distribution of aquaporin water channels AQP1 and AQP5 in the ductal system of the human pancreas", *Gut 52* (7), 1008-10116 (2003).
Griffin et al., "Delivery of Adeno-Associated-9 Vector to Newborn Pigs Transduces Genes in the Pancreas", North American Cystic Fibrosis Conference, Orlando, FL, AAV9 Abstract, 1 page (Oct. 11-13, 2012).
Griffin et al., "A Novel Gene Delivery Method Transduces Porcine Pancreatic Duct Epithelial Cells that Express CFTR", North American Cystic Fibrosis Conference, Salt Lake City, UT, AAV9 Abstract, 1 page (2013).
Griffin et al., "A Novel Gene Delivery Method Transduces Porcine Pancreatic Duct Epithelial Cells", *Gene Ther.* 21 (2), 123-130 (2014).
Inagaki et al., "Robust Systemic Transduction with AAV9 Vectors in Mice: Efficient Global Cardiac Gene Transfer Superior to that of AAV8", *Mol Ther 14* (1), 45-53 (2006).
Liu et al., "Rock inhibitor and feeder cells induce the conditional reprogramming of epithelial cells", *Am J. Pathol.* 180 (2), 599-607 (2012).
Loiler et al., "Targeting recombinant adeno-associated virus vectors to enhance gene transfer to pancreatic islets and liver", *Gene Ther.* 10(18), 1551-1558 (2003).
Marino et al., "Localization of the cystic fibrosis transmembrane conductance regulator in pancreas", *J. Clin. Invest.* 88 (2), 712-716 (1991).
McCarty, "Self-complementary AAV Vectors; Advances and Applications", *Mol. Ther.* 16(10), 1648-1656 (2008).
McClane et al., "Functional consequences of adenovirus-mediated murine pancreatic gene transfer", *Hum Gene Ther 8* (6), 739-746 (1997).
Meyerholz et al. "Pathology of gastrointestinal organis in procine model of cystic fibrosis", *Am. J. Pathol.* 176(3), 1377-1389 (2010).
Ostedgaard et al, "The DeltaF50-8 mutation causes CFTR misprocessing cystic fibrosis-like disease in pigs", *Sci Transl Med 3* (74), 74ra24 (2011).
Prasad et al., "Adeno-associated virus vector mediated gene transfer to pancreatic beta cells", *Gene Ther.* 7 (18), 1553-1561 (2000).
Raper et al., "Adenovirus-mediated in vivo gene transfer and expression in normal rat pancreas", *Pancreas* 12 (4), 401-410 (1996).
Rehman et al., "Efficient gene delivery to human and rodent islets with double-stranded (ds) AAV-based vectors", *Gene Ther 12* (17), 1313-1323 (2005).
Restrepo, et al., "A Novel Technique for Effective Transduction of AAV9-eGFP in The Pancreas", Oral presentation at Pediatric Academic Societies Annual Meeting Washington, DC, May 2013.
Restrepo, et al., "A Novel Gene Delivery Method Transduces Pancreatic Duct Epithelial Cells in Newborn Pigs", Pediatric Research Day, University of Iowa Hospitals and Clinics, Iowa City, IA, Mar. 2013.
Rogers et al., "Disruption of CFTR gene produces a model of cystic fibrosis in newborn pigs", *Science 321*, 1837-1841 (2008).
Stoltz et al., "Cystic fibrosis pigs develop lung disease and exhibit defective bacterial eradication at birth", *Sci Transl. Med.* 2(29), 29ra31 (2010).

(Continued)

*Primary Examiner* — Scott Long
(74) *Attorney, Agent, or Firm* — Viksnins Harris & Padys PLLP

(57) ABSTRACT

The present invention relates to a safe and effective way to deliver and express therapeutic compositions (e.g., transgenes) to the pancreas and lungs of a mammal.

17 Claims, 9 Drawing Sheets

(56) References Cited

OTHER PUBLICATIONS

Strong et al., "Localization of cystic fibrosis transmembrane conductance regulator mRNA in the human gastrointestinal tract by in situ hybridization", *J. Clin. Invest.* 93(1), 347-354 (1994).

Uc et al., "Pancreatic and biliary secretion are both altered in cystic fibrosis pigs", *Am. J. Physiol. Gastrointest Liver Physiol 303* (8), G961-8 (2012).

Uc et al., "A Novel Delivery Method to Transduce Genes in the Pancreas" American Pancreas Association of Pancreatology Joint Meeting, Miami, FL, Abstract, 1 page (Nov. 2012).

Wang et al., "Comparison of adenoviral and adeno-associated viral vectos for pancreatic gene delivery in vivo", *Hum Gene Ther.* 15 (8), 405-413 (2004).

Yang et al., "Glucose-responsive gene delivery in pancreatic Islet cells via recombinanat adeno-associated viral vectors", *Pharm. Res.* 17 (9), 1056-1061 (2000).

* cited by examiner

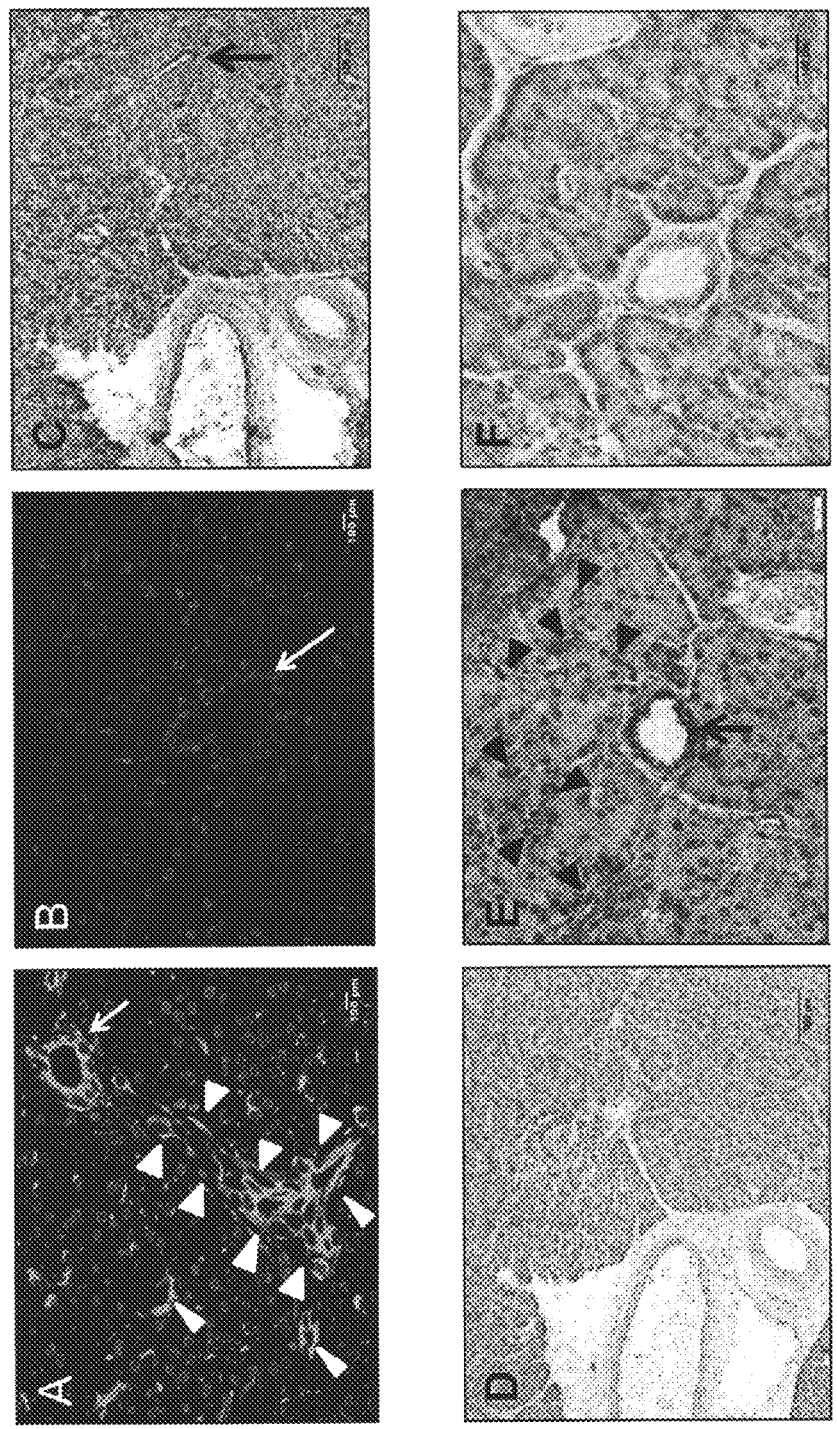
Figs. 4A-F

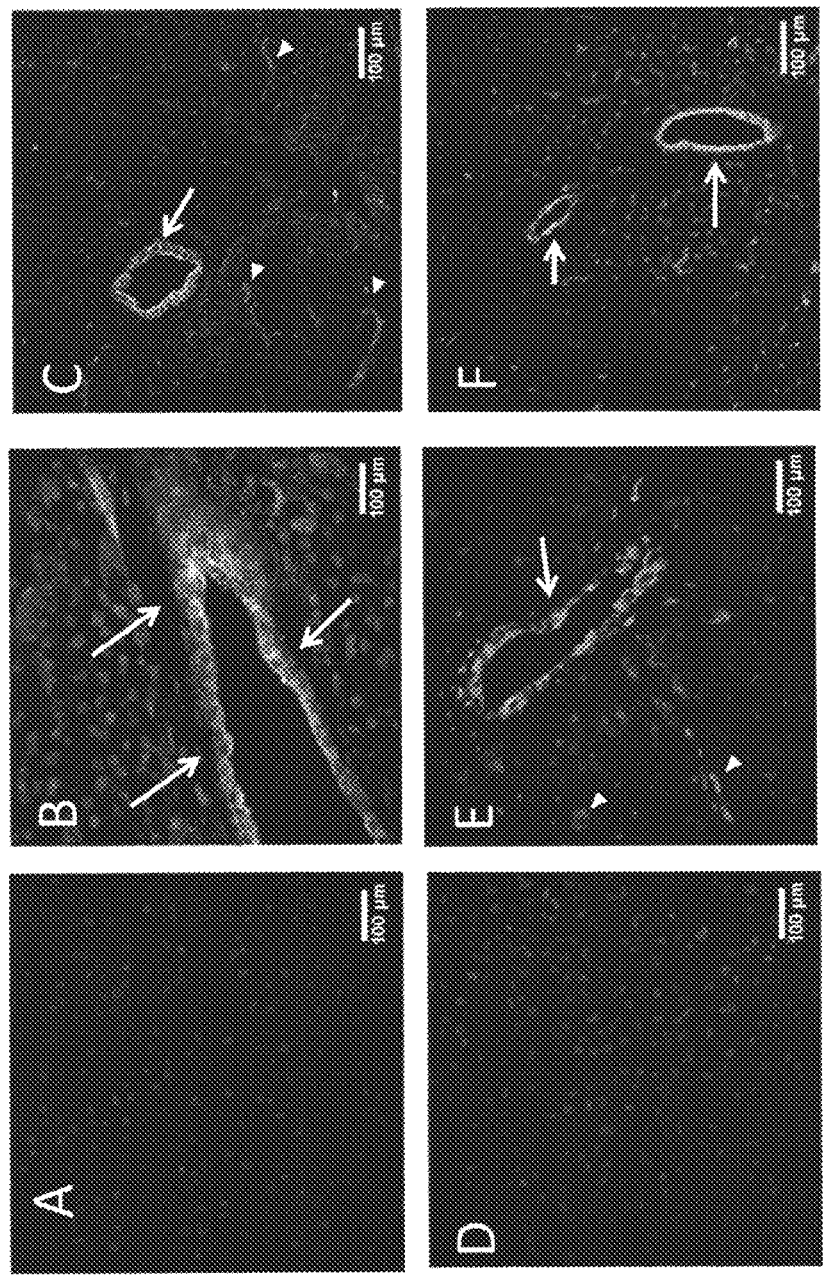

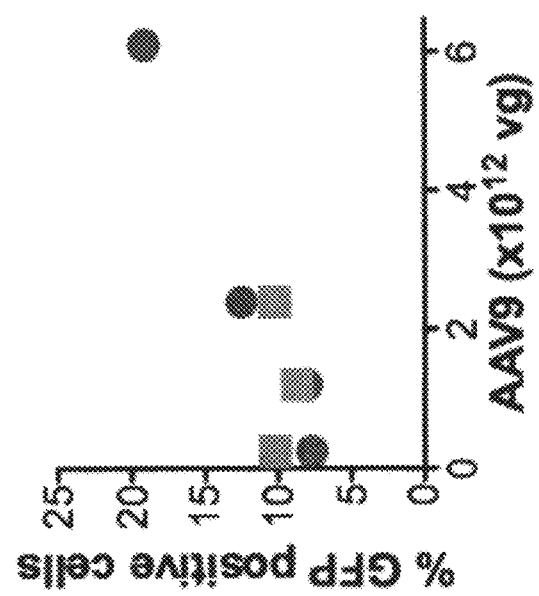

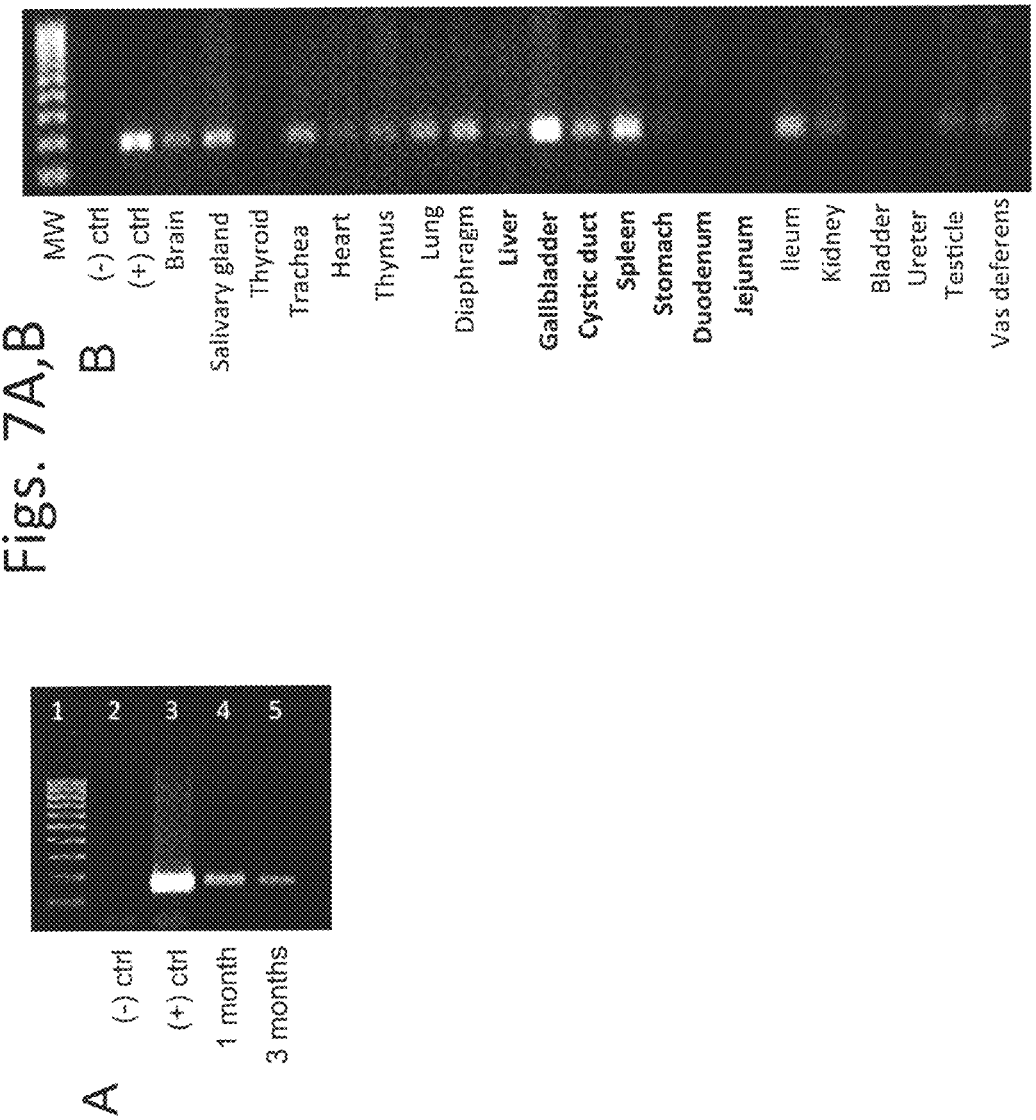
Figs. 7A, B

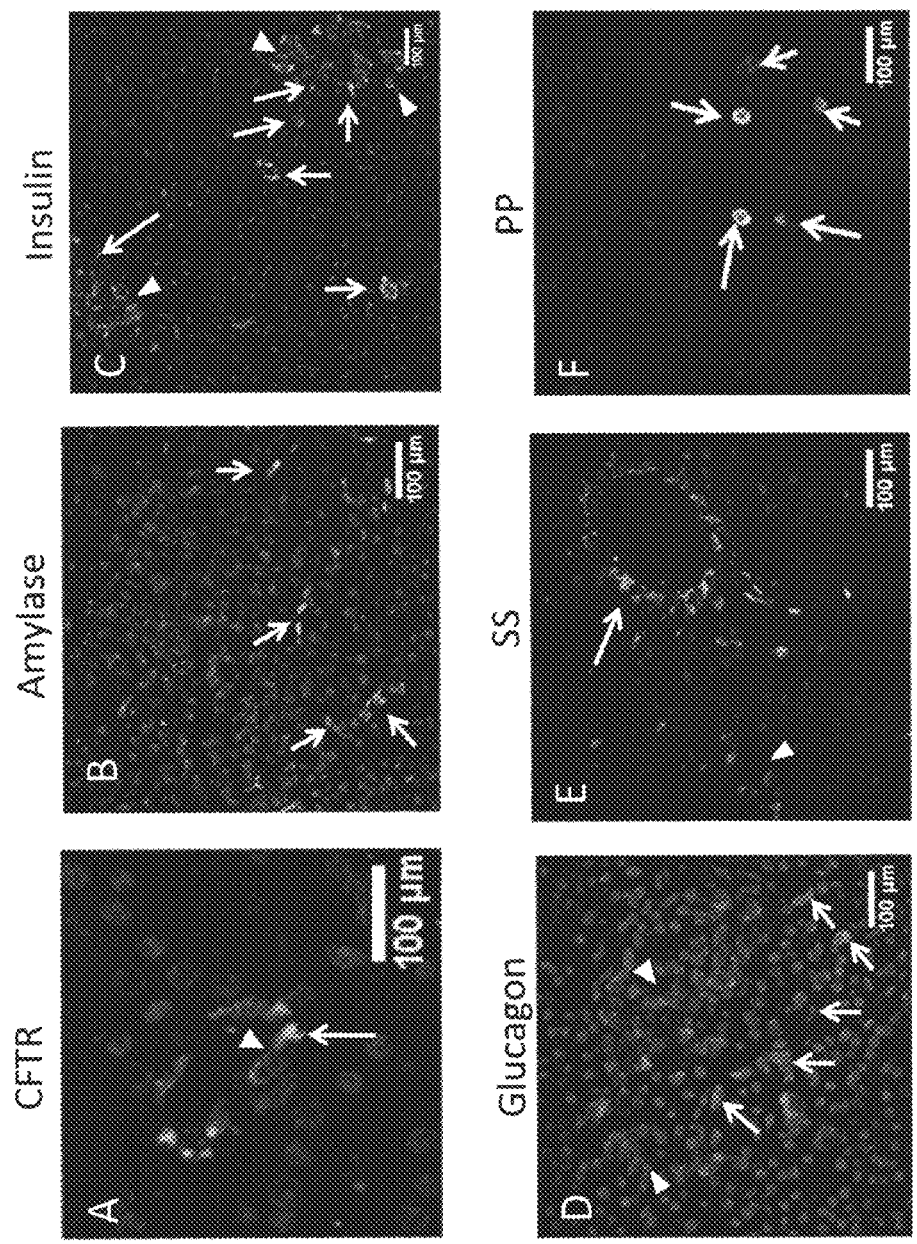
Figs. 8A-F

Figures 9A-C
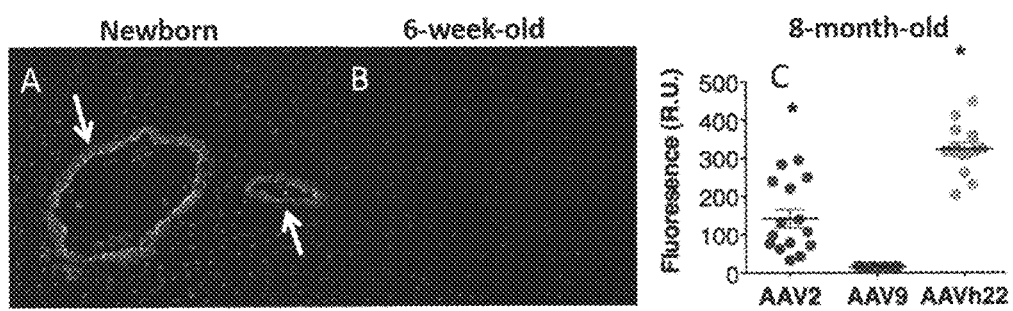
Figures 10A-10B
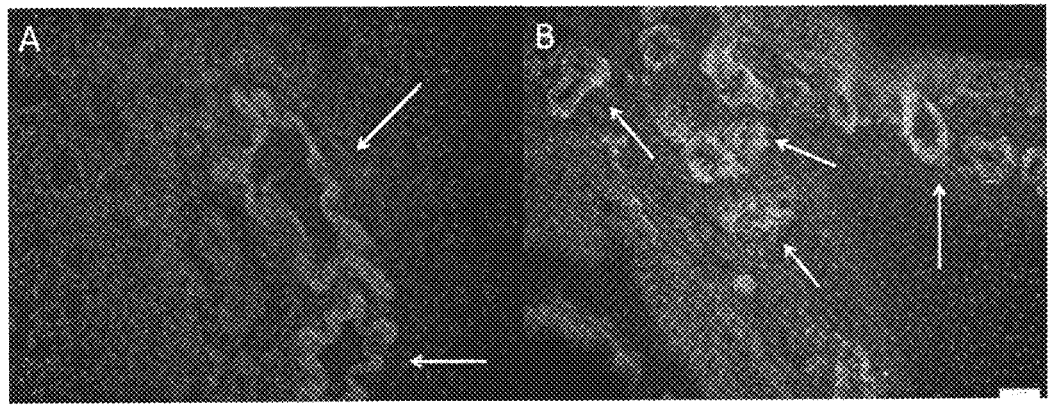

METHOD OF DELIVERING VECTORS TO PANCREAS AND LUNGS BY CANNULATING THE AORTA

CROSS-REFERENCE TO RELATED APPLICATIONS

This patent application claims the benefit of priority of U.S. provisional application Ser. No. 61/702,600, filed Sep. 18, 2012, and U.S. provisional application Ser. No. 61/792,901, filed Mar. 15, 2013, which applications are herein incorporated by reference.

FEDERAL GRANT SUPPORT

This invention was made with government support under Grant No. DK084049-01 awarded by the National Institutes of Health. The government has certain rights in the invention.

BACKGROUND OF THE INVENTION

Cystic Fibrosis (CF) is most commonly associated with its effects on the lungs those afflicted. In the lungs, the improperly functioning cystic fibrosis transmembrane conductance regulator (CFTR), which normally transports chloride ions across the lung membrane, results in increased mucous production, poor mucous clearance and a greater risk for contracting severe lung infections, which can ultimately cause death of the patient. Cystic fibrosis (CF) is caused by mutations in the gene encoding the cystic fibrosis transmembrane conductance regulator (CFTR). The pancreas is universally involved in CF with progression to pancreatic insufficiency in most cases within the first few years of life. Pancreatic insufficiency correlates with the severity of lung disease and CF-related diabetes (CFRD), therefore preserving pancreatic function in CF may have an important impact on disease morbidity and mortality. Pancreatic disease is universal in humans and pigs with cystic fibrosis (CF) and progresses to pancreatic insufficiency (PI) in a few years. CF is the most common form of PI in children.

Currently, there are no treatments to prevent the pancreatic disease progression in CF patients. Further, there are no gene therapy trials targeting the pancreas in CF or other pancreatic diseases. Moreover, in animal models, gene therapy techniques for pancreatic diseases suffer from the lack of effective and safe delivery methods.

SUMMARY OF THE INVENTION

In certain embodiments, the present invention provides a method of administering a therapeutic composition to a mammal in need thereof comprising: (a) inserting a catheter into an umbilical artery or femoral artery in the mammal, (b) advancing the catheter to the aorta (celiac or superior mesenteric artery branch), and (c) delivering a therapeutic composition through the catheter to the celiac or superior mesenteric artery branch in the mammal, wherein the therapeutic composition comprises is a vector encoding a nucleic acid encoding a therapeutic substance, and wherein the therapeutic composition is expressed in pancreas and/or lung tissue of the mammal.

In certain embodiments, the method further comprises (d) administering a saline flush after the administration of the therapeutic composition.

In certain embodiments, the therapeutic composition is expressed in pancreatic duct epithelial cells or pancreatic polypeptide secreting cells of islets. In certain embodiments, insulin, glucagon, somatostatin-secreting cells and acinar cells are not transduced.

In certain embodiments, the present invention provides a method of transducing epithelia in a pancreas in a mammal comprising: (a) inserting a catheter into an umbilical or femoral artery in the mammal to reach the aorta, (b) advancing the catheter to the aorta (celiac or superior mesenteric artery branches), and (c) delivering a therapeutic composition through the catheter to the celiac or superior mesenteric artery in the mammal, wherein the therapeutic composition comprises is a viral vector encoding a nucleic acid encoding a therapeutic substance, and wherein the therapeutic composition is expressed in the pancreas of the mammal. In certain embodiments, the method further transduces submucosal glands in a lung in the mammal. In certain embodiments, the therapeutic composition is expressed with a transduction efficiency of at least 1% in one or more of brain, salivary gland, trachea, heart, thymus, lung, diaphragm, liver, gallbladder wall, cystic duct, spleen, stomach, ileum, kidney, testicle, or vas deferens.

In certain embodiments, the present invention provides a method of transducing submucosal glands in a lung in a mammal comprising: (a) inserting a catheter into an umbilical or femoral artery in the mammal to reach the aorta, (b) advancing the catheter to the aorta (celiac or superior mesenteric artery branches), and (c) delivering a therapeutic composition through the catheter to the celiac or superior mesenteric artery in the mammal, wherein the therapeutic composition comprises is a viral vector encoding a nucleic acid encoding a therapeutic substance, and wherein the therapeutic composition is expressed in the submucosal glands in the lung of the mammal.

In certain embodiments, the present invention provides a method of treating pancreatic or lung disease in a mammal so as to treat the disease, the method comprising: (a) inserting a catheter into an umbilical or femoral artery in the mammal to reach the aorta, (b) advancing the catheter to the aorta (celiac or superior mesenteric artery branches), and (c) delivering a therapeutic composition through the catheter to the celiac or superior mesenteric artery in the mammal, wherein the therapeutic composition comprises an viral particle comprising a vector comprising a nucleic acid encoding a therapeutic protein, and wherein the therapeutic composition is expressed in pancreas and/or lung tissue of the mammal.

BRIEF DESCRIPTION OF DRAWINGS

FIGS. 4A-F. AAV9 transduces porcine ductal epithelial cells. Pancreas sections 30 days after newborn pigs received AAV9CMV.sceGFP (A, C, D, E, F) ($2.4 \times 10^{12}$ vg per animal) or vehicle (B) into the celiac artery. Immunofluorescence (A, B) and immunohistochemistry (C-F) images are shown. Arrows point to intralobular (larger) ducts, arrowheads point to intercalated (smaller) ducts. C and D; E and F are serial sections from the same animal, primary antibody is omitted in D and F. A, B$\times$20 mag; C, D$\times$10 mag, scale bar=100 μm; E, F$\times$60 mag, scale bar=20 μm.

FIGS. 5A-F: Delivery of AAV9 to the celiac artery in newborn pigs transduces the pancreatic ducts. Pancreas sections after newborn pigs received AAV9CMV.sceGFP (B, C, E, F) or vehicle (A, D) into the celiac artery. Immunofluorescence images are shown. (B, E) $1.2 \times 0^{12}$ vg; (F) $2.4 \times 0^{12}$ vg; (C) $6.1 \times 0^{12}$ vg; A-C euthanized after 1 month; D-F euthanized after 3 months. Arrows point to ducts, arrowheads point to intercalated ducts, scale bar=100 μm.

FIG. 6. AAV9 transduces ductal epithelial cells-time and dose response. Ten random pancreatic fields (20$\times$ mag) were assessed per animal (immunofluorescence). % GFP positive cells were calculated by counting GFP expressing divided by the total number of cells in the field (n=1 for all time points and doses except, n=2 for $6.1 \times 0^{12}$ vg at 1 month, and n=7 for $2.4 \times 0^{12}$ vg at 1 month). Circles: 1 month; Squares: 3 months.

FIGS. 7A,B. Celiac artery delivery of AAV9 vector leads to GFP expression in pancreas and several other tissues. (A) One and three months after delivery of AAV9CMV.sceGFP ($2.4 \times 0^{12}$ vg per animal) to the celiac artery in the newborn period, RNA was isolated from pancreas and end-point PCR was used to detect GFP mRNA. The results are representative of n=7 for one month exposure and n=1 for three-month exposure. Lane 1=ladder; lane 2=negative control; lane 3=positive control (10 ng GFP plasmid); lane 4=pancreas one month after delivery; lane 5=pancreas three months after delivery. (B). End-point PCR of tissues 30 days after injecting $2.4 \times 0^{12}$ vg AAV9CMV.sceGFP to the celiac artery of newborn pigs. MW: molecular weight ladder; (−) ctrl: negative control (sham animal); (+) ctrl: positive control (plasmid eGFP). Organs that receive arterial supply from celiac artery are in bold. The stomach and duodenum, two organs that receive blood supply from celiac artery were not transduced.

FIGS. 8A-F. AAV9 vector expression of GFP in CFTR-expressing duct cells. Immunofluorescent images of pancreas from pigs, 30 days after receiving $2.4 \times 0^{12}$ vg AAV9CMV.sceGFP in the newborn period. (A) anti-CFTR antibody for pancreatic ducts; (B) anti-amylase (arrowheads) for acinar cells; (C) anti-insulin (arrowheads) for β cells; (D) anti-glucagon (arrowheads) for α cells; (E) anti-somatostatin (SS) (arrowheads); (F) anti-pancreatic polypeptide (PP) (arrows indicating colocalization with eGFP); DAPI for nuclei. AAV9-GFP (arrows) was transduced in the cells that were expressing CFTR (arrowhead) on the apical side, A$\times$40 mag; B, C, D, E, F=$\times$20 mag. A, B, C, D, E=cells expressing GFP are shown with arrows.

FIGS. 9A-9C. AAV9 vector is not transduced in pigs after the newborn period. Immunofluorescence images of the pancreas one month after receiving $1.2 \times 10^{12}$ vg AAV9-GFP via celiac artery in (A) newborn (n=1) or (B) 6-week-old pigs (n=2). A and B were taken at the same exposure (10 s). GFP was transduced in newborn pig pancreas only, $\times$20 mag. (C) $10^4$ MOI of AAV9-GFP was applied to the basolateral side of pig airway epithelial cells obtained from 8-month-old pigs. Two weeks post-transfection, images were taken with fluorescent microscopy and quantified (20$\times$ field of view, N=15 each, *p<0.01 compared to AAV9). AAV9 did not transfect adult pig airway epithelia from basolateral side.

FIGS. 10A-10B. Adenovirus5-GFP-CFTR is expressed in pig airways following celiac artery injection. Immunofluorescence images of the pancreas 3 days after receiving $2 \times 10^{10}$ pfu Ad5-eGFP-CFTR via celiac artery in newborn pigs (n=2). (A) Arrows point to transduced airway epithelial cells, $\times$20 mag; (B) arrows point to submucosal glands, bar=50 μm.

DETAILED DESCRIPTION OF THE INVENTION

Figures 1A, 1B, 1C, 1D:
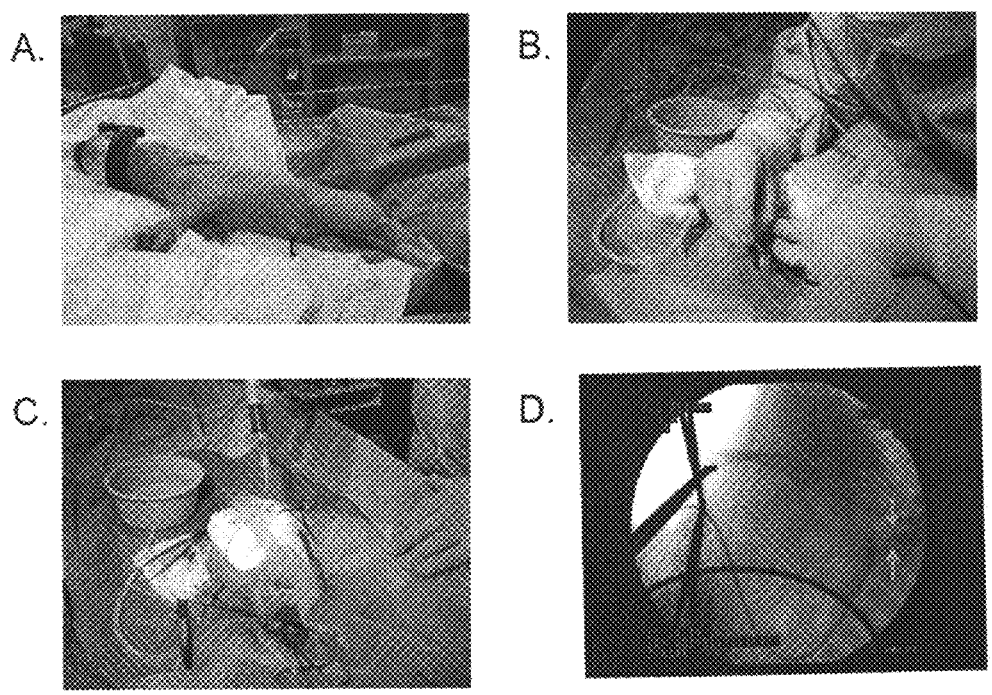
FIGS. 1A-1D. Transumbilical injection of celiac artery in newborn pig. A. Piglet was placed in right lateral decubitus position and received isofluorane via mask inhalation. B. Umbilical artery was identified and catheterized. C. After obtaining the arterial blood return, catheter was advanced into aorta and celiac artery. D. Location was verified with fluoroscopy and injection of the contrast to the celiac artery (arrows point to the celiac artery).

Cystic fibrosis is a respiratory disease caused by a genetic mutation of a single mutated gene (i.e., the cystic fibrosis transmembrane conductance regulator (CFTR) gene that encodes the protein CFTR). This disease could be better treated (e.g., controlled or cured) with improved gene therapy. For this to occur, advancements in gene therapy technology, such as increased transduction efficiency, increased levels of transgene expression, and increased length of transgene expression are important.

Gene therapy has the potential to cure CF, as it addresses the root cause of the disease, but gene transfer studies have not been done in humans with CF and other pancreatic diseases, because the current methods are ineffective and unsafe in rodent models. As CF mice do not develop pancreatic disease similar to humans, it is difficult to develop a gene transfer approach in this model. Pancreatic and airway histopathology and physiology are very similar between humans and pigs with CF; therefore the CF pig model creates an excellent opportunity for studying gene therapy in this model. Currently, gene therapy cannot be fully explored in the CF pig model because there are no studies showing the transduction efficiency of pig pancreas with gene transfer vectors.

The methods described herein may provide for increased numbers of transduced cells, increased and sustained transgene expression, increased expression level of transgene, increased length of transgene expression, increased likelihood for gene therapy success, and decreased immune response to gene therapy.

Vectors

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

The selection and optimization of a particular expression vector for expressing a specific therapeutic composition (e.g., a protein) in a cell can be accomplished by obtaining the nucleic acid sequence encoding the protein, possibly with one or more appropriate control regions (e.g., promoter, insertion sequence); preparing a vector construct comprising the vector into which is inserted the nucleic acid sequence encoding the protein; transfecting or transducing cultured cells in vitro with the vector construct; and determining whether the protein is present in the cultured cells.

Vectors for cell gene therapy include viruses, such as replication-deficient viruses. Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the target protein into the host cell genome, thereby permitting the nucleic acid sequence encoding the target protein to be passed on to the progeny of the cell when it divides. Promoter sequences in the LTR region have can enhance expression of an inserted coding sequence in a variety of cell types.

Another viral candidate useful as an expression vector for transformation of cells is an adenovirus (Ad), which is a double-stranded DNA virus. The adenovirus is infective in a wide range of cell types, including, for example, muscle and endothelial cells. Adenoviruses are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Examples of appropriate vectors include DNA viruses (e.g., adenoviruses), lentiviral, adeno-associated viral (AAV), poliovirus, HSV, or murine Moloney-based viral vectors, viral vectors derived from Harvey Sarcoma virus, ROUS Sarcoma virus, MPSV or hybrid transposon based vectors. In one embodiment, the vector is AAV. AAV is a small nonpathogenic virus of the parvoviridae family. AAV is distinct from the other members of this family by its dependence upon a helper virus for replication. The approximately 5 kb genome of AAV consists of one segment of single stranded DNA of either plus or minus polarity. The ends of the genome are short inverted terminal repeats which can fold into hairpin structures and serve as the origin of viral DNA replication. Physically, the parvovirus virion is non-enveloped and its icosohedral capsid is approximately 20 nm in diameter.

To-date many serologically distinct AAVs have been identified and have been isolated from humans or primates. For example, the genome of AAV2 is 4680 nucleotides in length and contains two open reading frames (ORFs). The left ORF encodes the non-structural Rep proteins, Rep 40, Rep 52, Rep 68 and Rep 78, which are involved in regulation of replication and transcription in addition to the production of single-stranded progeny genomes. Rep68/78 has also been shown to possess NTP binding activity as well as DNA and RNA helicase activities. The Rep proteins possess a nuclear localization signal as well as several potential phosphorylation sites. Mutation of one of these kinase sites resulted in a loss of replication activity.

The ends of the genome are short inverted terminal repeats (ITR) which have the potential to fold into T-shaped hairpin structures that serve as the origin of viral DNA replication. Within the ITR region two elements have been described which are central to the function of the ITR, a GAGC repeat motif and the terminal resolution site (trs). The repeat motif has been shown to bind Rep when the ITR is in either a linear or hairpin conformation. This binding serves to position Rep68/78 for cleavage at the trs which occurs in a site- and strand-specific manner. AAV vectors have several features that make it an attractive vector for gene transfer, such as possessing a broad host range, are capable of transduce both dividing and non-dividing cells in vitro and in vivo, and are capable of maintaining high levels of expression of transduced genes.

In certain embodiments, the viral vector is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight known serotypes of primate AAVs, AAV1 to AAV8. For example, serotype AAV9 is used to refer to an AAV which contains capsid proteins encoded from the cap gene of AAV9 and a genome containing 5' and 3' ITR sequences from the same AAV9 serotype. In certain embodiments, the AAV vector is AAV9.

The abbreviation "rAAV" refers to recombinant adeno-associated virus, also referred to as a recombinant AAV vector (or "rAAV vector"). In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art-recognized regions found at each end of the AAV genome which function together in cis as origins of DNA replication and as packaging signals for the virus.

The nucleotide sequences of AAV ITR regions are known. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector.

Nucleic acids encoding therapeutic compositions can be engineered into an AAV vector using standard ligation techniques, such as those described in Sambrook and Russell, Molecular Cloning: A Laboratory Manual, Cold Spring Harbor Laboratory Press Cold Spring Harbor, N.Y. (2001). For example, ligations can be accomplished in 20 mM Tris-Cl pH 7.5, 10 mM MgCl2, 10 mM DTT, 33 µg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs have been described in, e.g., U.S. Pat. No. 5,139,941. In particular, several AAV vectors are described therein which are available from the American Type Culture Collection ("ATCC") under Accession Numbers 53222, 53223, 53224, 53225 and 53226.

In certain embodiments, the adeno-associated virus packages a full-length genome, i.e., one that is approximately the same size as the native genome, and is not too big or too small. In certain embodiments the AAV is not a self-complementary AAV vector.

The viral vector further includes a promoter for controlling transcription of the heterologous gene. The promoter may be an inducible promoter for controlling transcription of the therapeutic composition. The expression system is suitable for administration to the mammalian recipient.

In certain embodiments, viral particles are administered. Viral particles are heat stable, resistant to solvents, detergents, changes in pH, temperature, and can be concentrated on CsCl gradients. AAV is not associated with any pathogenic event, and transduction with AAV vectors has not been found to induce any lasting negative effects on cell growth or differentiation. The ITRs have been shown to be the only cis elements required for packaging allowing for complete gutting of viral genes to create vector systems.

Nucleic Acids Encoding Therapeutic Composition

The present invention provides a method of administering a therapeutic composition. In certain embodiments, the therapeutic composition is a nucleic acid encoding cystic fibrosis transmembrane regulator protein (CFTR), Alpha 1 antitrypsin, ATP-binding cassette A3 protein (ABCA3), surfactant protein B (SFTPB) or surfactant protein C (SFTPC), green fluorescent protein (GFP), mCherry, cationic trypsinogen (PRSS1), pancreatic secretory trypsin inhibitor (PSTI), also known as serine protease inhibitor, Kazal type I (SPINK1), chymotrypsin-C (CTRC). In certain embodiments, the therapeutic composition is a nucleic acid encoding CFTR.

In certain embodiments, the therapeutic composition is a transgene, which is a gene encoding a polypeptide that is foreign to the retrovirus from which the vector is primarily derived and has a useful biological activity in the organism into which it is administered (e.g., a therapeutic gene). As used herein, the term "therapeutic gene" refers to a gene whose expression is desired in a cell to provide a therapeutic effect, e.g., to treat a disease.

Gene therapy may be used to successfully correct hereditary genetic errors. The molecular genetics of cystic fibrosis (CF) has been studied. Many CF patients carry a single amino acid deletion (F508) in one of the two nucleotide-binding domains in the CF transmembrane regulator (CFTR) protein. Other forms of genetic mutations in the CFTR genes have also been identified. This rich genetic information makes CF an ideal gene therapy candidate.

A nucleic acid encoding a therapeutic composition is "operably linked" when it is placed into a functional relationship with another nucleic acid sequence (e.g., the nucleic acid of the viral vector). Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accordance with conventional practice. Additionally, multiple copies of the nucleic acid encoding enzymes may be linked together in the expression vector. Such multiple nucleic acids may be separated by linkers.

Methods of Administration

In certain embodiments, the present invention provides a safe and effective way to deliver and express therapeutic compositions (e.g., transgenes) to the pancreas and lungs of a subject. Using this novel and minimally invasive technique, the trans-umbilical or trans-femoral artery approach, a vector encoding a therapeutic composition is delivered to the artery that supplies major branches to pancreas (celiac or superior mesenteric artery) of the subject.

The target cells for CF patients are undifferentiated, proliferating and differentiated, non-proliferating lung epithelial cells. For example, both the dividing and non-dividing lung epithelial cell types can be targeted by pseudotyped retroviral vectors carrying a wild type CFTR cDNA. Recent studies suggest that gene therapy may offer great benefits to CF patients even if only partial correction of CFTR gene function is achieved.

In certain embodiments, the present invention provides a method of administering a therapeutic composition to a mammal in need thereof comprising: (a) inserting a catheter into an umbilical or femoral artery in the mammal to reach the aorta, (b) advancing the catheter to the aorta (celiac or superior mesenteric artery branches), (c) delivering a therapeutic composition through the catheter to the celiac artery or superior mesenteric in the mammal, and (d) optionally, administering a saline flush after the administration of the therapeutic composition, wherein the therapeutic composition comprises is a vector (e.g., a viral vector) encoding a nucleic acid encoding a therapeutic substance, and wherein the therapeutic composition is expressed in pancreas and lung tissue of the mammal.

In certain embodiments, the viral vector is administered at a dose of at least $1.5 \times 10^{11}$ viral genomes. In certain embodiments, the viral vector is administered at a dose of at least $2.5 \times 10^{12}$ viral genomes. In certain embodiments, the viral vector is administered at a dose of at least $6.2 \times 10^{12}$ viral genomes. In certain embodiments, the therapeutic composition is expressed for more than 30 days (such as for more than 90 days) in the mammal. In certain embodiments, the therapeutic composition is expressed with a transduction efficiency of at least 15% in the lungs. In certain embodiments, the therapeutic composition is expressed with a transduction efficiency of at least 20% in pancreas. In certain embodiments, the therapeutic composition is expressed with a transduction efficiency of less than 1% in liver, stomach, spleen, heart, kidney, small intestine, colon, brain, thyroid, and/or vas deferens, as compared to the pancreas or lung.

In certain embodiments, the vector is administered to a subject that is a newborn (i.e., less than 8 weeks old, such as less than 6 weeks old). AAV9 has affinity for newborn pig lungs and pancreas, and the expression in other organs is negligible.

In certain embodiments, the mammal is a human. In certain embodiments, the mammal is a pig.

The invention will now be illustrated by the following non-limiting Examples.

Example 1

Delivery of Adeno-Associated-9 (AAV9) Vector to Newborn Pigs Transduces Genes in the Pancreas Using a novel and minimally invasive transumbilical catheterization technique, the inventors delivered a vector with a known affinity to pancreas, adeno-associated virus 9 (AAV9) to deliver the green fluorescent protein (self-complementary (sc) AAV9-eGFP) or sham vehicle control to the artery that supplies major branches to the pancreas (celiac artery) of wild-type newborn pigs (n=12). The inventors selected AAV9 as studies in other models have documented its remarkable ability to transduce a variety of organs. Three different doses were given ($2.5 \times 10^{11}$, $1.2 \times 10^{12}$, $2.5 \times 10^{12}$ or $6.2 \times 10^{12}$ vector genomes (vg)/animal) and results were evaluated at two time points (30 and 90 days). The pancreatic eGFP expression was determined with immunofluorescence, and morphometry was performed using ImageJ. At 90 days, eGFP expression was dose dependently and stably expressed in the centroacinar cells, intercalated, and intralobular ducts of the pancreas, co-localizing with CFTR expression, as well as in small and large interlobular pancreatic ducts. Ten random pancreatic fields (20× magnification) were assessed per animal with an average eGFP transduction of 20% ($2.5 \times 10^{12}$ vg dose). The histopathological assessment of tissues showed normal architecture with no inflammatory response. These results show the successful transduction of pancreatic cells by AAV9sc-eGFP. This process offers a novel and minimally invasive method for gene delivery that has the potential to be translated to humans with CF.

Specifically, newborn pigs were placed in the right lateral decubitus position, anesthetized using spontaneous mask ventilation with isoflurane and closely monitored (FIG. 1A). IV hydration was maintained with 10% dextrose infusion. Using sterile technique, a 3.5 Fr. single lumen arterial catheter (Kendall, Argyle, Tyco Healthcare Group, Mansfield, Mass.) was advanced into the umbilical artery (FIG. 1B). Free flow of arterial blood was obtained (FIG. 1C) and the catheter was flushed with saline. Position in the thoracic aorta was confirmed by fluoroscopy. Under fluoroscopic control, the catheter was exchanged over a 0.021" pre-wetted guide wire for a flushed 4 Fr. introducer. A 4 Fr. Cobra 1 (C1) Glidecath (Terumo Medical Corporation, New Jersey) was advanced over the wire and placed in the descending aorta. The catheter was slowly withdrawn below the diaphragm and the celiac artery was cannulated. Angiography confirmed selective cannulation (FIG. 1D). $2.5 \times 10^{11}$ or $1.2 \times 10^{12}$ or $2.5 \times 10^{12}$ vg scAAV9-eGFP or sham was injected into celiac artery and catheter was flushed with 5 ml normal saline. After the procedure, piglets recovered uneventfully and received standard care. Thirty and 90 days after the procedure, animals were sacrificed, lungs and pancreas were isolated.

Figures 2A, 2B, 2C:
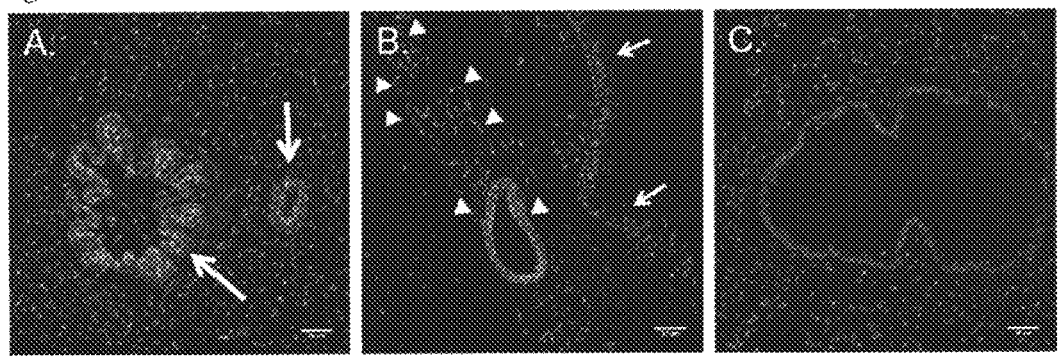
FIGS. 2A-2C. Lung expression of scAAV9-eGFP. Lungs were sectioned and stained with anti-GFP antibody and images were taken with fluorescent microscopy. eGFP was expressed in bronchiolar epithelial cells (A and B, arrows) and submucosal gland cells (B, arrowheads). Sham treated animal had no immunostaining (C); ×20 mag, scale bar: 20 µm.

Airway epithelial cells and submucosal gland cells express eGFP following injection of the vector to the celiac artery. Airways were sectioned and processed for hematoxylin stain and IFC. Tissues showed normal architecture without inflammatory cells, thus AAV9 did not induce an inflammatory response. Gene expression was dose-dependent and persisted 30 and 90 days after treatment. FIGS. 2A-C shows the airway transduction of a pig, 90 days after it received $2.5 \times 10^{12}$ vg vector. The measurements of eGFP (+) cells showed an average transduction efficiency of 15%. The expression of GFP was most prominent in the bronchioles and localized to surface epithelial cells and submucosal gland epithelia, control animals had no immunostaining.

Pancreatic duct epithelial cells express eGFP following injection of the vector to the celiac artery. Tissues were processed and stained as described above. There was normal architecture and no inflammatory cells in the pancreas of pigs that received the vector. Gene expression was dose-dependent and persisted 30 and 90 days after treatment. The expression was most prominent in the ductal structures, mainly intercalated and intralobular ducts that normally express CFTR. Controls had no immunostaining. The measurements of eGFP (+) cells showed an average transduction efficiency of 20%.

Example 2

Gene Delivery Method for Transducing Porcine Pancreatic Duct Epithelial Cells

Cystic Fibrosis (CF) is a multisystem disease caused by mutations in the gene encoding cystic fibrosis transmembrane conductance regulator (CFTR). CFTR is expressed in many epithelial cells, including pancreatic ducts, and functions as an apical membrane anion channel. Genetic mutations in CFTR determine the exocrine pancreatic function in CF. In patients with CF who carry two severe mutations that severely affect CFTR function, the pancreatic damage starts in utero. In these individuals, the damage continues after birth and they become pancreatic insufficient at young ages. Patients with sufficient pancreatic function carry a mild mutation on at least one allele and have residual CFTR activity (~10% of all CF patients). Patients with pancreatic sufficiency are prone to recurrent pancreatitis attacks and progressive decline in the exocrine pancreatic function as a consequence.

Despite treatment with pancreatic enzymes to prevent severe malnutrition, exocrine pancreatic insufficiency in CF tracks with delayed growth, accelerated progression of lung disease, and CF-related diabetes (CFRD); all associated with increased morbidity and mortality. Preserving the exocrine pancreatic function in CF may improve disease outcomes. Currently there are no treatments to prevent the pancreatic disease progression in CF. Designing therapies for CF pancreatic disease has been challenging because the pancreas is not easily accessible in humans, and mice models do not develop pancreatic disease typical of CF. Newborn CF pigs have pancreatic disease similar to patients with CF and the disease progresses over time, as it does in humans. Therefore the CF pig model creates an opportunity to study gene therapy for pancreatic disease. To date, there are no studies assessing the transduction of pig pancreas.

The available techniques to transduce cells in the pancreas of mice and rats (direct pancreatic injection, retrograde pancreaticobiliary duct delivery, or systemic delivery with temporary lamping of portal vein, hepatic artery, bile duct) are invasive, induce severe pancreatic inflammation and toxicity, and are not desirable for human studies. Other methods are ineffective: intravenous (IV) delivery of adenovirus vectors does not transduce pancreatic cells because the liver rapidly removes the virus from circulation. In general, adenoviral ectordirected gene transfer to the pancreas has been limited by inflammation and transient expression. AAV vectors are attractive because of their low immunogenicity, excellent safety record, and long-term transgene expression in non-dividing cells, even in the absence of genome integration. Still, the experience with delivering AAV vectors to the pancreas is limited. Also, the delivery methods are usually invasive and mainly transduce the acinar cells and islets of mice, not the pancreatic duct epithelial cells where CFTR is expressed. This work successfully expressed genes in the pancreatic duct epithelial cells of WT pigs. AAV9 vector delivery via the celiac artery, the vessel that supplies major branches to the pancreas, efficiently and stably transduced pancreatic duct epithelial cells. This is the first study showing expression of transgenes in pig pancreatic duct cells.

Results

IV Injection of the AAV9 Vector does not Transduce Pancreas in Pigs.

The present work targeted the pancreas and primarily CFTR-expressing pancreatic duct epithelial cells, using an efficient and minimally invasive technique. Pigs were chosen because CF pigs lacking the CFTR function exhibit defective anion transport and replicate the multisystem disease observed in humans with CF, including pancreatic disease (Rogers C S, Stoltz D A, Meyerholz D K, Ostedgaard L S, Rokhlina T, Taft P J et al. Disruption of the CFTR gene produces a model of cystic fibrosis in newborn pigs. *Science* 2008; 321(5897): 1837-1841; Stoltz D A, Meyerholz D K, Pezzulo A A, Ramachandran S, Rogan M P, Davis G J et al. Cystic fibrosis pigs develop lung disease and exhibit defective bacterial eradication at birth. *Sci. Transl. Med.* 2010; 2(29): 29ra31; Ostedgaard L S, Meyerholz D K, Chen J H, Pezzulo A A, Karp P H, Rokhlina T et al. The DeltaF508 mutation causes CFTR misprocessing and cystic fibrosis-like disease in pigs. *Sci Transl Med* 2011; 3(74): 74ra24; Abu-El-Haija M, Ramachandran S, Meyerholz D K, Griffin M, Giriyappa R L, Stoltz D A et al. Pancreatic damage in fetal and newborn cystic fibrosis pigs involves the activation of inflammatory and remodeling pathways. *Am J Pathol* 2012; 181(2): 499-507; Meyerholz D K, Stoltz D A, Pezzulo A A, Welsh M J. Pathology of gastrointestinal organs in a porcine model of cystic fibrosis. *Am J Pathol* 2010; 176(3): 1377-89; Uc A, Giriyappa R, Meyerholz D K, Griffin M, Ostedgaard L S, Tang X X et al. Pancreatic and biliary secretion are both altered in cystic fibrosis pigs. *Am J Physiol Gastrointest Liver Physiol* 2012; 303(8): G961-8.)

AAV9CMV.sceGFP ($2.4 \times 10^{12}$ viral genome particles (vg) per animal, n=2) was delivered intravenously (ear vein) to 1-day-old pigs and we observed no gene transfer to the pancreas, one month after the injection (data not shown). Therefore, systemic venous delivery did not transduce the pancreas in newborn pigs.

Injection of the Celiac Artery as a Novel Method to Deliver Transgenes to the Pancreas of Newborn Pigs.

Figure 3:
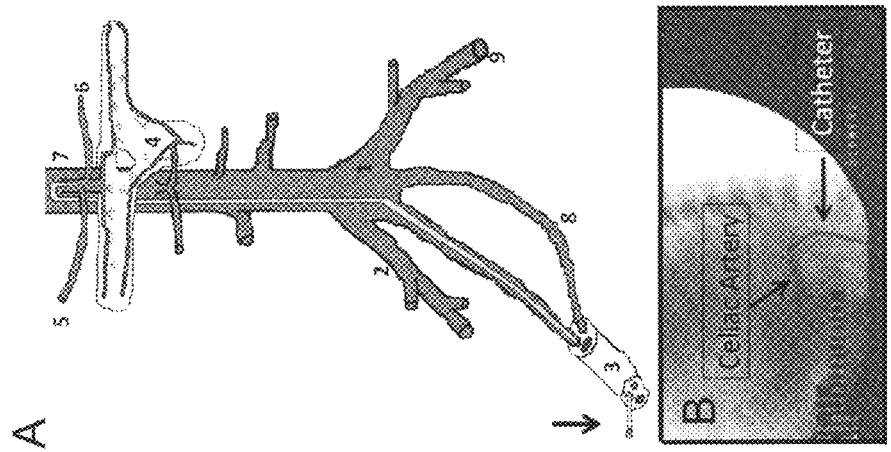
FIGS. 3A,B. Celiac artery catheterization via umbilical arteries. (A) In newborns, celiac artery can be reached by placing a catheter (arrow, green) into the umbilical arteries, which connect to the aorta. The catheter is then advanced to the celiac artery. (1) aorta; (2) right iliac artery; (3) umbilical cord (1 vein and two arteries); (4) pancreas; (5) hepatic artery; (6) splenic artery; (7) celiac artery with catheter; (8) umbilical artery; (9) left femoral artery. (B) Angiography confirming cannulation of the celiac artery (arrows). Vector or vehicle was injected and the catheter was flushed with normal saline.

Vector delivery was assessed via the celiac artery, the vessel that supplies major branches to the pancreas in humans and pigs. Shortly after birth (24-48 h), the celiac artery can be easily accessed via the umbilical arteries (FIGS. 3A,B). The AAV9 vector was administered to the celiac artery of newborn pigs and all pigs tolerated the procedure well without complications. After the procedure, piglets recovered uneventfully and received standard care.

AAV9 Gene Delivery Via Celiac Artery Did not Induce Pancreatic Inflammation in Pigs.

Adenoviral vector-directed gene transfer to the pancreas is limited by inflammation and transient expression of the genes in rodents (Raper S E, DeMatteo R P. Adenovirus-mediated in vivo gene transfer and expression in normal rat pancreas. *Pancreas* 1996; 12(4): 401-10; McClane S J, Hamilton T E, Burke C V, Raper S E. Functional consequences of adenovirus-mediated murine pancreatic gene transfer. *Hum Gene Ther* 1997; 8(6): 739-46; Wang A Y, Peng P D, Ehrhardt A, Storm T A, Kay M A. Comparison of adenoviral and adeno-associated viral vectors for pancreatic gene delivery in vivo. *Hum Gene Ther* 2004; 15(4): 405-13; Ayuso E, Chillon M, Agudo J, Haurigot V, Bosch A, Carretero A et al. In vivo gene transfer to pancreatic beta cells by systemic delivery of adenoviral vectors. *Hum Gene Ther* 2004; 15(8): 805-12), but AAV vectors typically have low immunogenicity. To determine whether AAV9 caused an immunogenic response in pigs, their activity level, food intake, and weight gain was monitored on a daily basis. No differences were observed between vector and vehicle-treated pigs. One and 3 months after vector delivery, animals were euthanized and pancreata isolated. The pancreatic histology of pigs that received AAV9 at birth was examined and compared to the control pigs. The pancreas had normal architecture with no infiltrating inflammatory cells after vector delivery.

GFP is Expressed in Porcine Pancreatic Duct Epithelial Cells Following AAV9 Vector Delivery to the Celiac Artery.

Although AAV vectors have been used to target other organ systems, there is limited information on their delivery to the pancreas. In general, gene transfer to the pancreas has been done in vitro and/or on islet cells of rodents (Prasad K M, Yang Z, Bleich D, Nadler J L. Adeno-associated virus vector mediated gene transfer to pancreatic beta cells. *Gene Ther.* 2000; 7(18): 1553-1561; Yang Y W, Kotin R M. Glucose-responsive gene delivery in pancreatic Islet cells via recombinant adeno-associated viral vectors. *Pharm Res* 2000; 17(9): 1056-61; Loiler S A, Conlon T J, Song S, Tang Q, Warrington K H, Agarwal A et al. Targeting recombinant adeno-associated virus vectors to enhance gene transfer to pancreatic islets and liver. *Gene Ther* 2003; 10(18): 1551-8; Rehman K K, Wang Z, Bottino R, Balamurugan A N, Trucco M, Li J et al. Efficient gene delivery to human and rodent islets with double-stranded (ds) AAV-based vectors. *Gene Ther* 2005; 12(17): 1313-23). There are no data reported using AAV vectors in pigs. To determine whether the GFP reporter gene was expressed in pancreatic duct cells following the delivery of AAV9 vector to the celiac artery of newborn pigs, immunofluorescence, immunohistochemistry (IHC), and RT-PCR were used. FIGS. 4A-4F summarize the findings in pigs euthanized 1 month after receiving $2.4 \times 10^{12}$ vg of AAV9CMV.sceGFP (n=7) or vehicle per animal. FIGS. 5A-F shows immunofluorescence images from pigs that received various doses of the AAV9 vector or vehicle and followed for 1 to 3 months. One month after delivering the AAV9 vector to the celiac artery, GFP expression was found in pig pancreatic ducts, including the intercalated and intralobular ducts (FIGS. 4A, C, E; FIGS. 5A-F) that normally have high levels of CFTR (Burghardt B, Elkaer M L, Kwon T H, Racz G Z, Varga G, Steward M C et al. Distribution of aquaporin water channels AQP1 and AQP5 in the ductal system of the human pancreas. *Gut* 2003; 52(7): 1008-1016; Marino C R, Matovcik L M, Gorelick F S, Cohn J A. Localization of the cystic fibrosis transmembrane conductance regulator in pancreas. *J. Clin. Invest* 1991; 88(2): 712-716; Strong T V, Boehm K, Collins F S. Localization of cystic fibrosis transmembrane conductance regulator mRNA in the human gastrointestinal tract by in situ hybridization. *J. Clin. Invest* 1994; 93(1): 347-354). There was no staining detected if the primary antibody was omitted (IHC) (FIG. 4D, F), confirming that the antibody staining was specific to GFP. Vehicle-treated animals were not immunoreactive for GFP (FIG. 4B). Gene expression was dose-dependent and persisted 3 months after treatment (last time point tested) (FIG. 6). GFP expression shown by immunofluorescence and immunohistochemistry in pig pancreas was confirmed with PCR both at 1- and 3-month time points (FIG. 7A). Transduction was detected in ~10% of the cells of the pancreas, predominantly ductal epithelial cells, 2 months after delivery of the AAV9CMV.eGFP vector (non-self complimentary form), using $2.4 \times 10^{12}$ vg (n=3). Thus, the delivery of AAV9 vector to the celiac artery in newborn pigs effectively transduces the pancreatic duct epithelial cells.

AAV9 Vector Delivered to the Celiac Artery of Newborn Pigs Transduces CFTR Expressing Pancreatic Duct Epithelial Cells.

Studies in human and pig samples have shown that CFTR is expressed at high levels in the pancreas and localizes to the pancreatic duct epithelia. To determine whether GFP was expressed in CFTR-expressing pancreatic duct epithelial cells following AAV9 delivery, CFTR in transduced tissues was immunolocalized (FIG. 8A). CFTR was expressed on the apical side of duct epithelia and CFTR and GFP co-localized within the same cells. These results confirm that our technique transduces CFTR-expressing duct cells in the pancreas.

AAV9 Vector Transduces Pancreatic Polypeptide-Secreting Cells of the Islets.

AAV9 transduces β cells and to lesser degree α cells in mice, but it is not known if porcine pancreatic cells are susceptible to AAV9 transduction. To examine the pancreatic cell subtypes transduced with our technique, pancreas sections were immunostained with antibodies against amylase (acinar cell marker) (FIG. 8B), insulin (β cell marker) (FIG. 8C), glucagon (α cell marker) (FIG. 8D), somatostatin (δ cell marker) (FIG. 8E), and pancreatic polypeptide (PP cell marker) (FIG. 8F). Colocalization was detected only with PP cells. These results suggest that the celiac artery injection of AAV9 does not transduce pancreatic acinar cells and only tranduces PP cells of the islets.

Delivering the AAV9 Vector to the Celiac Artery Transduces Other Organs.

Because the present technique involves a systemic injection of a vector with a CMV promoter, other organs could also be transduced. The celiac artery supplies blood to the stomach, duodenum, spleen, liver, gallbladder, and the vector may also enter the systemic circulation and reach other organs. To determine whether other organs were also transduced following the celiac artery injection of the AAV9CMV.sceGFP vector, we performed end-point RT-PCR for GFP 30 days after the injection. The organs that are transduced by our technique are shown in FIG. 7B. The liver, gallbladder, cystic duct, and spleen receive blood supply from the celiac artery and were transduced by our technique. Interestingly, the organs that receive the blood supply from celiac artery, such as stomach and duodenum were not transduced. The transduction of other organs (salivary gland, trachea, lung, vas deferens, ileum) typically involved in CF may be advantageous for treating this systemic disease.

Discussion

In this study, we describe a novel, safe, and minimally invasive gene delivery technique to efficiently express a reporter gene in the pancreatic duct epithelial cells of pigs, an animal species that has a CF model available. This is the first study showing efficient transduction of pig pancreas with a gene transfer vector.

The pancreas is a retroperitoneal organ and difficult to access. The techniques that deliver genes to the pancreas of mice and rats involve injecting the pancreatic parenchyma or the pancreatic duct or giving it systemically in conjunction with laparotomy and clamping the portal vein, the hepatic artery, or the bile duct. These methods are invasive and are not easily translated to humans. A major advantage of our technique is the ease with which it is performed.

Because the umbilical artery is patent in newborn pigs for 24-48 h after birth, it allows easy, noninvasive (no surgical cutdown needed) access to the aorta, celiac artery, and the pancreatic arterial supply. Umbilical artery catheterization is commonly performed in humans; and is well tolerated by even premature, very low birth weight neonates. Once the umbilical vessels are no longer accessible, the celiac artery can be catheterized via the femoral artery. Therefore, our method has the potential to be translated to humans.

In general, viral vectors delivered to the venous system do not efficiently transduce the pancreas. This is probably because the vector is removed from the circulation before it reaches the pancreas. Indeed, we have not observed pancreatic gene expression following the IV delivery of the vector. Our technique circumvents this problem by directly delivering the vector to the arterial blood supply of the pancreas, using a minimally invasive approach. The technique is well-tolerated by the animals and leads to efficient transgene expression, 1 and 3 months after delivery.

Inflammation and transient transgene expression have been the major problems with delivering adenoviral vectors to the pancreas. Inflammation has not been observed with AAV vectors, although the experience with delivering AAV vectors to the pancreas is limited. We observed no pancreatic inflammation in our model 1 and 3 months after gene delivery, confirming that the AAV vectors are suitable for use in pancreatic gene transfer studies.

There is limited information on delivering AAV vectors to the pancreas. In general, gene transfer studies to the pancreas have been done in vitro and/or on islet cells of rodents. Serotypes 1, 2, 5, 6, and 8 have been used in vitro and in vivo in mouse pancreas, with AAV8 and 9 showing most promise. Transduction of ductal cells has been reported in mouse pancreas with AAV6 and AAV8, but the vectors were delivered via pancreatic duct or direct pancreatic injection. The colocalization of the transgene with CFTR was also not examined. Our studies confirm that AAV serotype 9 is an efficient vector to transduce the pancreas.

Previous studies with AAV delivery to the mouse pancreas reported AAV transduction of acinar cells and islets (mainly β cells), not the pancreatic duct cells where CFTR is expressed. Delivering transgenes to CFTR-expressing pancreatic ducts is a novel and exciting finding of this study. This method has the potential to transfer CFTR gene to the pancreas of humans with CF. In addition, this approach might be used to target genes that control cell proliferation and survival in humans with pancreatic ductal adenocarcinoma, or have applications for other genetic or acquired diseases of the pancreas.

Another interesting finding of this study is the expression of transgenes in pancreatic polypeptide-expressing cells. While the exact physiological role of PP is not determined, the plasma levels of this hormone are reduced in humans with CF and in patients who develop diabetes secondary to chronic pancreatitis. The lack of a PP response to hypoglycemia or secretin confirms the exocrine pancreatic dysfunction in humans with CF. It is not known whether PP plays a role in CF-related diabetes.

In summary, the present example provides a novel, efficient and well-tolerated gene delivery technique to the pancreatic duct epithelial cells of a large animal species that has a CF model available.

Materials and Methods

Virus Preparation

AAV9CMV.sceGFP (self-complementary genome) or AAV9CMV.eGFP were produced by triple-plasmid co-transfection of human HEK 293 cells and purified by Mustang Q membrane cassettes after iodixanol gradient centrifugation. The vectors were dialyzed using 7,000 MWCO Slide-A-Lyzer Mini Dialysis Units (pierce Cat #69560 (10 μl-100 μl) Rockford, Ill., USA), in a 1000:1 buffer (HyClone Cat # RR10417.01) to sample ratio. The dialysis unit was then placed in a flotation device and dialyzed at 4° C. for 60 minutes using a low speed setting on a stir plate. The sample was collected and kept on ice until delivery.

Animal Procedures

All studies were approved by the University of Iowa Animal Care and Use Committee. Newborn pigs (*Sus scrofa*) were obtained during the first 24 h of life, when the umbilical cord was still present. The procedure was performed by an interventional pediatric cardiologist. He had previously developed a minimally invasive and innovative method for transcatheter intervention of the ductus arteriosus by cannulating the umbilical artery in newborn pigs. We modified this technique by selectively cannulating the celiac artery, which is the vessel that supplies major branches to the pancreas in humans and pigs. Shortly after birth (24-48 h), the celiac artery can be easily accessed via the umbilical arteries that extend into the umbilical cord (FIG. 3A).

Piglets were anesthetized using spontaneous mask ventilation with isoflurane. Pulse oximetry, breath $CO_2$, heart rate, and body temperature were monitored throughout the procedure. IV hydration was maintained with 10% dextrose infusion through a peripheral vein. Animal was placed in the right lateral decubitus position. The entire procedure was performed under sterile technique. A previously flushed 3.5 Fr. single lumen arterial catheter (Kendall, Argyle, Tyco Healthcare Group, Mansfield, Mass., USA) was advanced into the umbilical artery to 20 cm, free flow of arterial blood was obtained and the catheter was flushed with saline. Position in the thoracic aorta was confirmed by fluoroscopy. Under fluoroscopic control the catheter was exchanged over a 0.021" pre-wetted guide wire (Argon Medical Devices, Inc. Athens, Tex., USA) for a flushed 4 Fr. Introducer (Cordis, Johnson & Johnson, Miami, Fla., USA). The dilator was removed and a 4 Fr. Cobra 1 (C1) Glidecath (Terumo Medical Corporation, New Jersey, USA) was advanced over the wire and placed in the descending aorta. The catheter was flushed with saline after removing the wire. The catheter was slowly withdrawn below the diaphragm and the celiac artery was cannulated. Angiography confirmed the cannulation (FIG. 3B). AAV9CMV.sceGFP ($2.4\times10^{11}$ vg per animal; $1.2\times10^{12}$ vg per animal; $2.4\times10^{12}$ vg per animal; $6.1\times10^{12}$ vg per animal; n=1 for all time points and doses except, n=2 for $6.1\times10^{12}$ vg at 1 month, n=7 for $2.4\times10^{12}$ vg at 1 month) or AAV9CMV.eGFP ($2.4\times10^{12}$ vg per animal; n=3 at 2 months) were injected into the celiac artery and the catheter was flushed again with 5 ml normal saline. The vehicle was given to 2 animals as control and they were sacrificed at 1 and 3 months.

After the procedure, piglets recovered uneventfully and received standard care. During the first 24 hours, the piglets were fed colostrum supplement (Manna Pro, Saint Louis, Mo., USA) via syringe every 2 hours followed by milk replacer (Multi-species Milk Replacer, Carpentersville, Ill., USA) via syringe every 4 hours until competent to feed independently. The piglets were transitioned to pelleted feed at ~2 weeks of age. One and 3 months after vector delivery, animals were euthanized using intracardiac Euthasol® injection (90 mg/kg), followed by bilateral thoracotomy. The animals were not kept beyond 3 months of age, because they become very large (>100 lbs) and challenging to handle in the animal care facility.

Necropsy and Tissue Harvesting

One or three months after injection, the animals were sedated with intramuscular (IM) injection of Ketamine (20 mg/kg) and Xylazine (0.2-2.2 mg/kg) and euthanized as described above. A full necropsy was performed and tissues were collected. Tissues were placed in 4% paraformaldehyde (PFA) and fixed for 24-48 hours. Following fixation, tissues were either processed and paraffin embedded or placed through a series of sucrose gradients (10%, 20%, and 30%) for cryoprotection and snap frozen.

Immunohistochemistry (IHC) Staining

Frozen tissue sections were cut (10 μm) and fixed in 10% ice-cold zinc formalin for 5' and washed with dH2O, Sections were then immersed in Phosphate Buffer Solution (PBS) for 5' and transferred into 0.2% Triton-X for 10 minutes for permeabilization. Sections were washed in PBSx3 for 5 minutes each. Endogenous peroxidase activity was quenched in 3% hydrogen peroxide ($H_2O_2$) at for 8' and washed in PBSx3 for 5' each. Sections were blocked in 5% normal goat serum for 30' at room temperature (RT) and incubated at RT with primary (rabbit polyclonal anti-GFP, 1:400) for 1 h, followed by secondary antibody (Envision plus Rabbit) for 30'. Signal development was performed using a chromogen diaminobenzidine (DAB) solution for 10 minutes and washed in running tap water for 10'. Tissues were counterstained in Harris Hematoxylin for 20", transferred back under the running tap water for 5 minutes, dehydrated through graded alcohols, cleared in xylenes, and mounted.

Immunofluorescence (IF) Staining

Frozen tissue sections were cut (10 μm) and fixed in 10% cold Z-fix for 5'. Sections were washed in tap water and then placed in three washes of PBS for 5' each. Tissues were permeabilized in 0.2% Triton X-100 for 10' and washed in PBSx3. Nonspecific background staining was blocked using a 5% normal goat serum for 30'. Sections were incubated with primary antibody 1:400 anti-GFP (Abcam GR8 722-1, Cambridge, Mass., USA) at 4° C. overnight, followed with secondary antibody (Alexa-flour 488) for 30' at RT. Slides were washed with PBSx3, mounted with Vectashield and DAPI. Ten random pancreatic fields (20× mag) were assessed per animal and % GFP positive cells were calculated by counting GFP expressing divided by the total number of cells in the field.

End-Point RT-PCR

End-point RT-PCR was performed as a confirmation of GFP presence from tissues collected during necropsy, snap frozen in liquid nitrogen, and stored at −80° C. The tissues were homogenized (no. 03-392-106 grinder, 0.5 mL pestle size; Fisher Scientific, Pittsburgh, Pa., USA) and RNA was extracted using Qiagen RNeasy Lipid Tissue Kit (no. 74084; Qiagen) with the optional DNase digestion step performed to prevent genomic DNA contamination. Following RNA extraction, all samples were measured for RNA concentration using NanoDrop 1000 (Thermo Scientific, Rockford, Ill., USA). Samples were randomly selected to obtain RNA integrity numbers (RIN) using Agilent 2100 bioanalyzer system (Agilent Technologies, Santa Clara, Calif., USA). RIN numbers ranged from 7.4-9.2, indicating minimally degraded RNA suitable for downstream applications. Reverse-Transcriptase RT-PCR was performed using SuperScript® VILO™ Master Mix (Cat. No. 11755050, Invitrogen, Grand Island, N.Y., USA), 1000 ng starting RNA concentration, and UltraPure™ RNase/DNase-Free distilled water (Cat. No. 10977015, Invitrogen, Grand Island, N.Y., USA). The thermal cycler (Product No. PTC-1148C, Bio-Rad, Hercules, Calif., USA) settings were 25° C. for 10 minutes, 42° C. for one hour, and 85° C. for 5 minutes. End-point RT-PCR was then performed on the cDNA synthesized using HotStartTaq Master Mix Kit (Cat. No. 203446, Qiagen, Valencia, Calif., USA), 10 mM eGFP forward primer 5'-ACG TAA ACG GCC ACA AGT TC-3', 10 mM eGFP reverse primer 5'-AAG TAG TGC TGC TTC ATG TG-3' (Integrated DNA Technologies, Coralville, Iowa, USA). A 1.5% agarose gel was prepared and samples run at 120 v for 30 minutes.

Statistics:

To measure transduction efficiency, ten random pancreatic fields (20× mag) were assessed for all time points and concentrations (immunofluorescence) (n=1 for all time points and doses except, n=2 for $6.1 \times 10^{12}$ vg at 1 month, and n=7 for $2.4 \times 10^{12}$ vg at 1 month). % GFP positive cells were calculated by counting GFP-expressing cells divided by the total number of cells in the field. Data were presented as the average of individual data points.

Example 3

Transduction of Pancreatic Duct Cells in Older Animals

It was explored whether it was possible to transduce pancreatic duct cells in older animals with the present technique. Because the umbilical artery is closed after the first 1-2 days of life, we used the femoral artery to catheterize the aorta and reach the celiac artery in 6-week-old pigs. No gene transfer was found with this method in older animals (FIGS. 9A,B). Interestingly, AAV9 vector did not transduce the pig airway epithelia of older pigs if applied basolaterally, compared to other AAV vectors (FIG. 9C).

To determine the extent of gene transduction following celiac artery injection of AAV9-GFP, all organs except pancreas were harvested after 30 days and end-point PCR for GFP was performed. The results show that GFP was transduced in the brain, salivary gland, trachea, heart, thymus, lung, diaphragm, liver, gallbladder wall, cystic duct, spleen, stomach, ileum, kidney, testicle, and vas deferens of WT pigs. Negative results were seen for thyroid, duodenum, jejunum, bladder and ureter. The transduction of genes in organs typically involved in CF may be an advantage in treating this systemic disease with the present technique.

Transduction of pancreas was not seen following delivery of AAV2-H22-eGFP (1 month) and Adenovirus5-eGFP (3 days) to the celiac artery in newborn pigs. Lung epithelial cells and submucosal gland cells were transduced following delivery of Adenovirus5-eGFP-CFTR to the celiac artery in newborn pigs (3 days) (FIGS. 10A,B), suggesting that CFTR delivered via this technique will be expressed in the lung epithelia and appropriately trafficked to the apical side of the cells.

Example 4

Adenoviral Gene Transfer Corrects the Ion Transport Defect in the Pancreatic Duct Epithelia of a Porcine Cystic Fibrosis Model Gene therapy offers great promise to cure pancreatic diseases of genetic origin, such as Cystic Fibrosis (CF). But gene therapy studies have never targeted the pancreas in humans with CF or other pancreatic diseases, because gene transfer methods to rodents were either ineffective, invasive or associated with severe complications (Raper S E, DeMatteo R P. Adenovirus-mediated in vivo gene transfer and expression in normal rat pancreas. Pancreas 1996; 12(4): 401-10; McClane S J, Hamilton T E, Burke C V, Raper S E. Functional consequences of adenovirus-mediated murine pancreatic gene transfer. Hum Gene Ther 1997; 8(6): 739-46; Wang A Y, Peng P D, Ehrhardt A, Storm T A, Kay M A. Comparison of adenoviral and adeno-associated viral vectors for pancreatic gene delivery in vivo. Hum Gene Ther 2004; 15(4): 405-13; Ayuso E, Chillon M, Agudo J, Haurigot V, Bosch A, Carretero A et al. In vivo gene transfer to pancreatic beta cells by systemic delivery of adenoviral vectors. Hum Gene Ther 2004; 15(8): 805-12). A novel and minimally invasive technique was used to deliver the AAV9 vector to the celiac artery of newborn pigs and transduced genes in the pancreatic duct epithelial cells where CFTR is normally expressed.

In this work, the CFTR gene was transferred to an in vitro model of CF pancreatic duct epithelia to test whether it was possible to transduce the cells and correct the cyclic-AMP mediated ion transport defect.

In general, pancreatic duct cells are very difficult to grow and propagate in culture. To isolate the CF and non-CF pancreatic duct epithelial cells, a method was followed that was recently described by Liu et al. (Liu X, Ory V, Chapman S, Yuan H, Albanese C, Kallakury B et al. ROCK inhibitor and feeder cells induce the conditional reprogramming of epithelial cells. *Am J Pathol* 2012; 180(2): 599-607). This method extends the life span of epithelial cells using both fibroblast feeder cells and a Rho-associated kinase (ROCK) inhibitor, Y-27632.21 for an indefinite period of time. Briefly, the CF and non-CF newborn pig pancreas was excised, followed by collagenase digestion and microdissection of pancreatic ducts. Microdissected ducts were placed on growth media floated on filter rafts and incubated overnight at 37° C., 5% $CO_2$. the ducts were identified by swelling. Briefly, the swollen ducts were opened using a micropipette and cocultured with ROCK inhibitor and feeder fibroblast cells. Pancreata were harvested from CFTR+/+, −/−, deltaF508/deltaF508 (df/df) pigs. Cells isolated from pancreas were plated on a feeder layer of irradiated (3000 rad) Swiss 3T3 cells (J2 subclone) and grown in medium containing 10 μM ROCK inhibitor (Y-27632). Small colonies could be observed after 1 day. At day 5, there were large islands of epithelial cells that compressed the surrounding feeder cells. After passaging for 3-4 times, cells were seeded on semi-permeable filters and cultured for 7-10 days before further experiments.

It was investigated whether the electrophysiology between CF and non-CF porcine duct epithelial cells were different. Short-circuit currents (Isc), and transepithelial conductance (Gt) were measured. Transport was altered with: (i) amiloride, which inhibits the apical epithelial sodium channel; (ii) forskolin and 3-isobutyl-2-methylxanthine (IBMX), which increase cAMP levels leading to phosphorylation of CFTR by cAMP-dependent protein kinase; and (iii) GlyH-101, which inhibits the CFTR channel.

Figure 11:
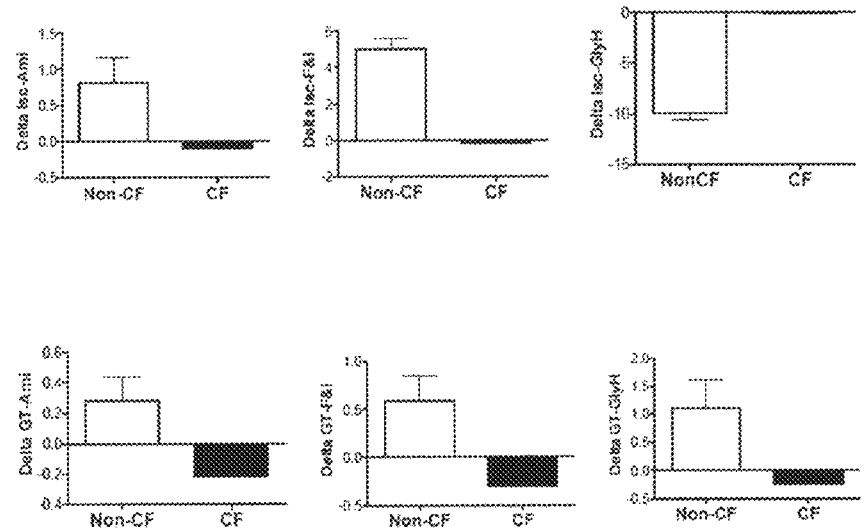
FIG. 11. CF pancreatic duct epithelia lack cAMP-regulated anion transport. Results show changes in Isc and Gt following amiloride (100 μM), cAMP agonists 10 μM forskolin and 100 μM 3-isobutyl-2-methylxanthine (F&I), 100 μM GlyH-101 (GlyH) in non-CF and CF pancreatic duct cultures. Studies performed on 7 different non-CF and 1 CF cultures.

Short-circuit current (Isc) was measured and found that there was no response to the cAMP-stimulant F&I (delta IscF&I) or CFTR inhibitor (delta IscGlyH). The response to amiloride was not increased (FIG. 11). It was found that the conductance (Gt) in CF was also decreased. These data show that CF pancreatic duct epithelia lack cAMP-regulated anion transport.

It was then asked whether it was possible to transfer CFTR to the pancreatic duct epithelia of CF pigs. An adenoviral vector was used that expressed GFP-labeled CFTR (Ad5/GFPCFTR) to transduce porcine pancreatic duct epithelial cultures. At 72-96 hours after infection, the epithelial cultures were fixed and GFP fluorescence imaged with immunofluorescence microscope. Briefly, CFTR−/− pig pancreatic duct epithelial cells were treated with Ad5/GFPCFTR MOI 100 or vehicle from the basolateral side. Three-to-four days after treatment, cells were fixed and immunofluorescence images were obtained. No GFP-positive cells were found in control epithelia, but epithelial cells transduced with Ad5/GFP-CFTR expressed GFP-positive cells. These data suggest that Ad5/GFP-CFTR transduces pancreatic duct epithelia.

Figure 12:
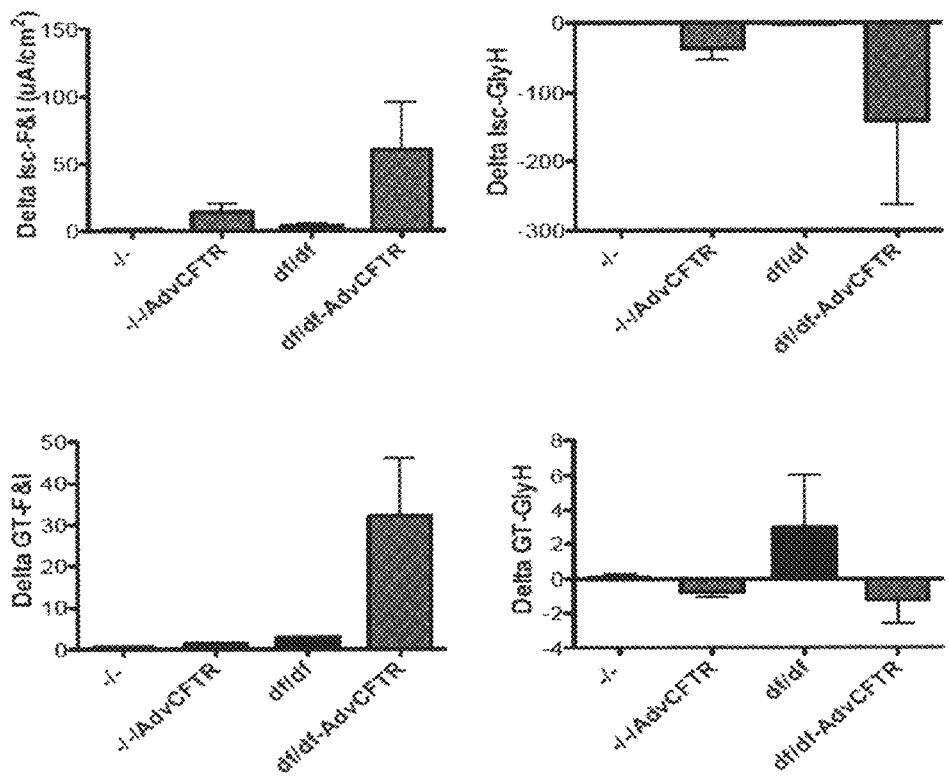
FIG. 12. Ad5/GFP-CFTR restores cAMP-stimulated anion transport in CF cells. CFTR−/− and CFTR df/df cells were treated with Ad5/GFP-CFTR at 100 MOI and Isc and Gt were measured 72-96 h after treatment. Change in current (Isc, top panels) and conductance (lower panels) after adding cAMP agonists 10 μM forskolin and 100 μM 3-isobutyl-2-methylxanthine (F&I). CFTR−/− (n=3); CFTR−/− Ad5/GFP-CFTR-treated (n=5); CFTR df/df (n=2); CFTR df/df Ad5/GFP-CFTR-treated (n=2).

It was further investigated whether Ad5/GFP-CFTR vector could correct the cAMP-regulated anion transport in CF pancreatic duct epithelial cells. CF epithelia were transduced with AdGFP-CFTR at an MOI of 100. It was found that CF epithelia transduced with 100 MOI of AdGFP-CFTR demonstrated a significant increase in ΔIscF&I and ΔGtF&I (FIG. 12). These results show that CF pancreatic duct epithelia transduced with AdGFP-CFTR restore the c-AMP induced anion transport. The present data suggest that the CFTR gene transfer to the pancreatic duct cells is feasible in vitro and potentially in vivo.

Adeno-associated virus serotype 9 (AAV9) was used in the present mode, because intravenous (IV) delivery of adenovirus vectors does not transduce pancreatic cells in other animal models. To determine whether AAV9 can transduce pancreatic ducts in vitro, pancreatic duct cells were treated with AAV9-GFP $5 \times 10^{-4}$ M four days after seeding. 3-4 days later, CFTR expression was tested with immunofluorescence. These results show that the pancreatic duct epithelial cells in CF pigs can be transduced with AAV9.

Taken together, these data show that CF porcine pancreatic duct cells show defective cyclic AMP-regulated anion transport and CFTR gene transfer rescues the ion transport phenotype.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of administering a therapeutic composition to a mammal in need thereof comprising:
    (a) inserting a catheter into an umbilical or femoral artery in the mammal,
    (b) advancing the catheter to the aorta (celiac or superior mesenteric artery), and
    (c) delivering a therapeutic composition through the catheter to the celiac or superior mesenteric artery in the mammal,
    wherein the therapeutic composition is an adeno-associated viral-9 (AAV9) vector encoding a nucleic acid encoding a therapeutic substance, and wherein the therapeutic substance is expressed in pancreatic duct epithelial cells or pancreatic polypeptide secreting cells of islets of the mammal, and wherein insulin, glucagon, somatostatin-secreting cells and acinar cells are not transduced in the mammal.

2. The method of claim 1, further comprising:
    (d) administering a saline flush after the administration of the therapeutic composition.

3. The method of claim 1, wherein the viral vector is administered at a dose of at least $1.5 \times 10^{11}$ viral genomes.

4. The method of claim 1, wherein the viral vector is administered at a dose of at least $2.5 \times 10^{12}$ viral genomes.

5. The method of claim 1, wherein the viral vector is administered at a dose of at least $6.2 \times 10^{12}$ viral genomes.

6. The method of claim 1, wherein the therapeutic substance is CFTR.

7. The method of claim 1, wherein the therapeutic composition is expressed for more than 30 days in the mammal.

8. The method of claim 1, wherein the therapeutic composition is expressed for more than 90 days in the mammal.

9. The method of claim 1, wherein the therapeutic composition is expressed with a transduction efficiency of at least 15% in the lungs.

10. The method of claim 1, wherein the therapeutic composition is expressed with a transduction efficiency of at least 20% in pancreas.

11. The method of claim 1, wherein the therapeutic composition is expressed with a transduction efficiency of less than 1% in liver, stomach, spleen, heart, kidney, small intestine, colon, brain, thyroid, and/or vas deferens as compared to the pancreas or lung.

12. The method of claim 1, wherein the therapeutic composition is expressed with a transduction efficiency of at least 1% in one or more of brain, salivary gland, trachea, heart, thymus, lung, diaphragm, liver, gallbladder wall, cystic duct, spleen, stomach, ileum, kidney, testicle, or vas deferens.

13. A method of treating pancreatic or lung disease in a mammal so as to treat the disease, the method comprising:
   (a) inserting a catheter into an umbilical or femoral artery in the mammal to reach the aorta,
   (b) advancing the catheter to the aorta (celiac or superior mesenteric artery), and
   (c) delivering a therapeutic composition through the catheter to the celiac or superior mesenteric artery in the mammal,
      wherein the therapeutic composition is an adeno-associated viral-9 (AAV9) viral particle comprising a vector comprising a nucleic acid encoding a therapeutic substance, and wherein the therapeutic substance is expressed in pancreatic duct epithelial cells or pancreatic polypeptide secreting cells of islets of the mammal, and wherein insulin, glucagon, somatostatin-secreting cells and acinar cells are not transduced in the mammal.

14. The method of claim 13, wherein the method treats pancreatic disease in a mammal by transducing pancreatic epithelia in the mammal, and wherein the therapeutic composition is expressed in the pancreas of the mammal.

15. The method of claim 14, wherein the method further transduces lung submucosal glands in the mammal.

16. The method of claim 15, wherein the method treats lung disease in a mammal by transducing lung submucosal glands in the mammal, and wherein the therapeutic composition is expressed in the submucosal glands in the lung of the mammal.

17. The method of claim 1, wherein the catheter is inserted into an umbilical artery.

* * * * *